United States Patent [19]
Wunderer et al.

[11] Patent Number: 6,026,681
[45] Date of Patent: Feb. 22, 2000

[54] DEVICE AND PROCESS FOR DETERMINING THE STIFFNESS OF SHEET-LIKE ARTICLES SUCH AS BANK NOTES

[75] Inventors: Bernd Wunderer, Munich; Ulrich Schanda, Holzkirchen, both of Germany

[73] Assignee: Giesecke & Devrient GmbH, Munich, Germany

[21] Appl. No.: 08/875,105

[22] PCT Filed: Nov. 22, 1996

[86] PCT No.: PCT/EP96/05175

§ 371 Date: Sep. 12, 1997

§ 102(e) Date: Sep. 12, 1997

[87] PCT Pub. No.: WO97/19425

PCT Pub. Date: May 29, 1995

[30] Foreign Application Priority Data

Nov. 23, 1995 [DE] Germany .................. 195 43 674

[51] Int. Cl.[7] ............................................. G01L 5/04
[52] U.S. Cl. ............................. 73/159; 73/801; 73/587
[58] Field of Search .......................... 73/159, 801, 587, 73/593, 660

[56] References Cited

U.S. PATENT DOCUMENTS

| | | | |
|---|---|---|---|
| 3,894,732 | 7/1975 | Müller | 271/10 |
| 4,073,007 | 2/1978 | Boivin | 73/627 |
| 4,463,607 | 8/1984 | Hilton | 73/159 |
| 4,519,249 | 5/1985 | Hunt | 73/159 |
| 5,089,776 | 2/1992 | Furukawa et al. | 73/159 |
| 5,201,424 | 4/1993 | Hain | 73/159 |
| 5,297,062 | 3/1994 | Cresson et al. | 73/159 |
| 5,808,199 | 9/1998 | Kazys et al. | 73/159 |
| 5,813,277 | 9/1998 | Schmidt et al. | 73/159 |

*Primary Examiner*—Hezron Williams
*Assistant Examiner*—Thuy Vinh Tran
*Attorney, Agent, or Firm*—Bacon & Thomas, PLLC

[57] ABSTRACT

The apparatus for determining the stiffness of sheet material is provided with mechanical means which periodically touch the sheet material, causing it to vibrate. The sounds produced by the vibration are detected by a detector. From the detected sounds an evaluating device determines the stiffness of the sheet material. The sheet material is held or guided in a transport device such that it can yield to the mechanical action within certain limits in the area of contact without being irreversibly deformed.

13 Claims, 5 Drawing Sheets

DEVICE AND PROCESS FOR DETERMINING THE STIFFNESS OF SHEET-LIKE ARTICLES SUCH AS BANK NOTES

BACKGROUND OF THE INVENTION

1. Field of the Invention

This invention relates to an apparatus and method for determining the stiffness of sheet material such as bank notes.

2. Discussion of Related Art

Such an apparatus is known from EP-A 0 073 133. In this apparatus the sheet material is guided between two flat belts in the middle and deflected via a double-conical roller by an angle of 180°. Simultaneously the sheet material is deformed in the longitudinal and transverse directions. The sounds produced during this process are detected by a microphone. From the detected sounds an evaluating device determines the stiffness of the sheet material.

A disadvantage of the apparatus is that the produced sounds decrease greatly when the stiffness of a sheet is measured several times. The stiffness of the sheet material lessens with each measuring process due to the deformation involved in the measuring process.

Starting out from this, the invention is based on the problem of proposing an apparatus and method for determining the stiffness of sheet material where the stiffness of the sheet material remains essentially unchanged.

SUMMARY OF THE INVENTION

The basic idea of the invention is essentially to produce sounds by mechanical means which periodically touch the sheet material, causing it to vibrate. The sounds produced by the vibrations are then detected by a detector. From the detected sounds an evaluating device determines the stiffness of the sheet material. Since the volume of the produced sounds is approximately proportional to the stiffness of the sheet material, the volume of the produced sounds is a direct measure of stiffness of the sheet material.

The sheet material is held or guided in a transport device such that it can yield to the mechanical action within certain limits in the area of contact without being irreversibly deformed.

An advantage of the invention is that the stiffness of the sheet material remains virtually unchanged. Even when the stiffness of a sheet is determined several times the intensity of the produced sounds remains essentially the same. The reproducibility of the intensity of the produced sounds is on the average at least 95%.

In a preferred embodiment of the invention the mechanical means have a rotating roll with a certain number of corners. The corners are disposed in rotational symmetry on the roll. The sheet material is transported through the apparatus by a transport device, and the driving axle of the rotating roll is disposed perpendicular to the transport direction of the sheet material. The direction of rotation of the rotating roll is in the direction of transport. The rotary frequency of the rotating roll is selected such that the circumferential speed dependent on the rotary frequency and the radius of the roll is greater than or equal to the transport speed of the sheet material.

BRIEF DESCRIPTION OF THE DRAWINGS

In the following, various embodiments of the invention will be described with reference to the figures, in which.

DETAILED DESCRIPTION

Figure 1:
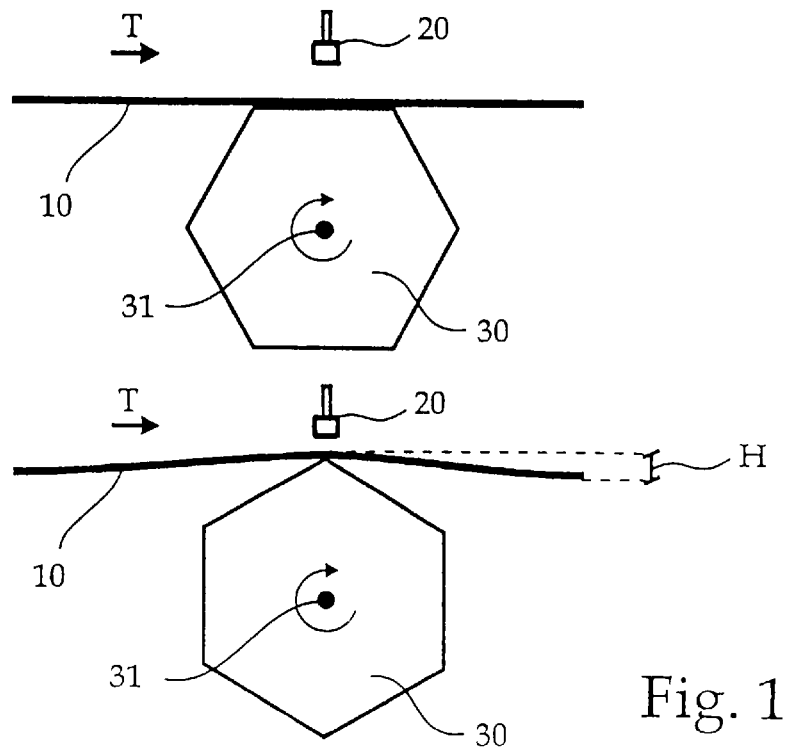
FIG. 1 shows a schematic diagram of a preferred embodiment.

FIG. 1 shows a schematic diagram of a preferred embodiment of the invention is a side view. Sheet material 10 is transported through the apparatus in direction of transport T for example by means of transport belts, which are initially not shown here for reasons of clarity. The mechanical means shown here for producing sounds are rotating roll 30 with six rotationally symmetric corners. Driving axle 31 of rotating roll 30 is aligned perpendicular to transport direction T of the sheet material. A detector 20 detects the sounds produced.

The direction of rotation of roll 30 is in transport direction T of the sheet material. The rotary frequency of roll 30 is selected such that the circumferential speed of roll 30 dependent on the rotary frequency and the radius of roll 30 is greater than or equal to the transport speed of the sheet material. This selection of rotary frequency and direction of rotation prevents the sheet material transported through the apparatus from hitting a corner of the roll and being slowed down. Such a slowdown would increase the danger of jamming in the transport system. In principle the operation of the apparatus can also be ensured upon a change of direction of rotation or rotary frequency of roll 30.

Due to the rotation of roll 30 the corners periodically touch sheet material 10, causing it to vibrate. The sheet material is thereby raised in the area of roll 30 by lifting height H. Lifting height H is a measure of the volume of the produced sounds.

The radius of roll 30, number N of the corners and the rotary frequency of roll 30 are the parameters by means of which the preferred embodiment of the invention can be optimally adapted to the particular apparatus-related boundary conditions, such as maximum spatial extent of the apparatus. The contact frequency of the roll on sheet material 10 results from the product of rotary frequency and number of corners. Lifting height H depends on the selected roll radius and number of corners.

Figure 2:
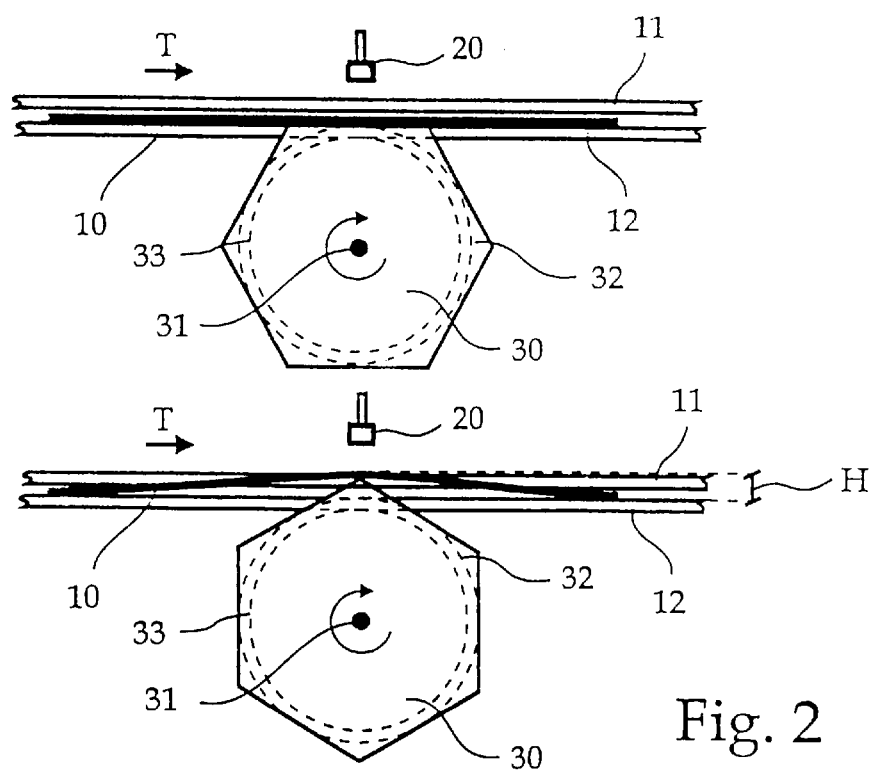
FIG. 2 shows a schematic diagram of the preferred embodiment with transport belts.
Figure 3:
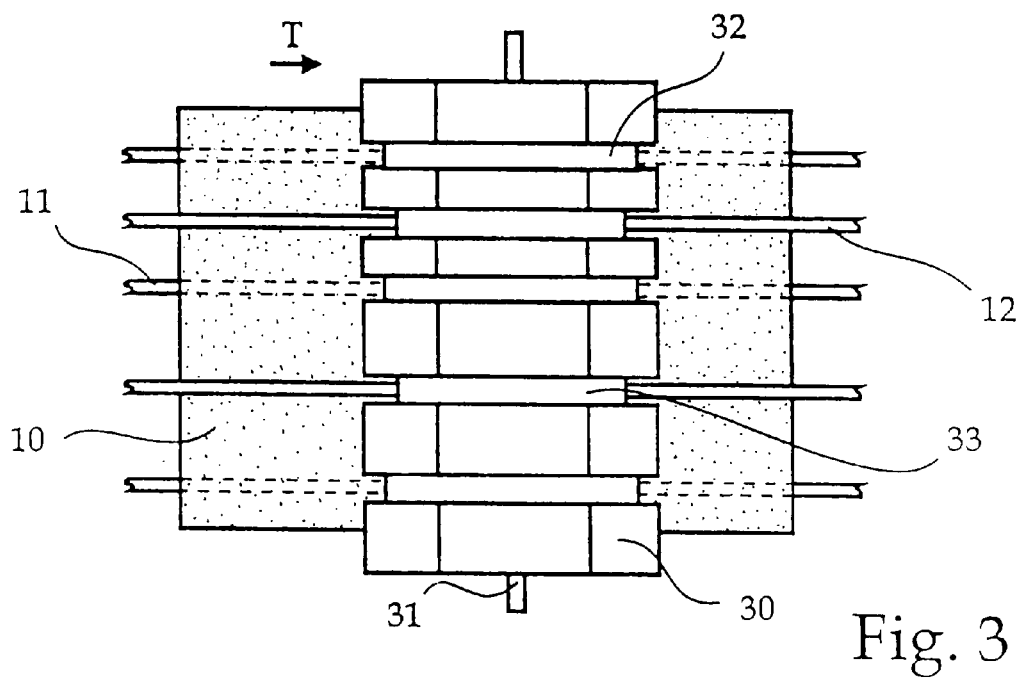
FIG. 3 shows a schematic diagram of the preferred embodiment with transport belts from below.

FIG. 2 and FIG. 3 show the preferred embodiment with a transport device in a side view and from below, the transport device being integrated into hexagonal roll 30. The transport device has three upper transport belts 11 and two lower transport belts 12 between which sheet material 10 is clamped for transport through the apparatus.

To avoid interactions between rotating roll 30 and upper transport belts 11 or lower transport belts 12, free-running rollers 32, 33 across which the corresponding transport belts are guided are provide din the roll. These rollers can be decoupled from driving axle 31 for example by corresponding ball bearings so that transport belts 11 and 12 can be moved at constant transport speed independently of the circumferential speed of roll 30. The radius of free-running rollers 32 is preferably selected equal to the radius of the incircle of roll 30. The radius of free-running rollers 33 is preferably selected smaller than the radius of the incircle of hexagonal roll 30. If no sheet material 10 is present the upper edges of lower transport belts 12 and the lower edges of upper transport belts 11 are flush with roll 30 in the position of roll 30 according to the upper part of FIG. 1. The contact of roll 30 with sheet material 10 takes place in the areas between transports belt 11 and 12.

Figure 4:
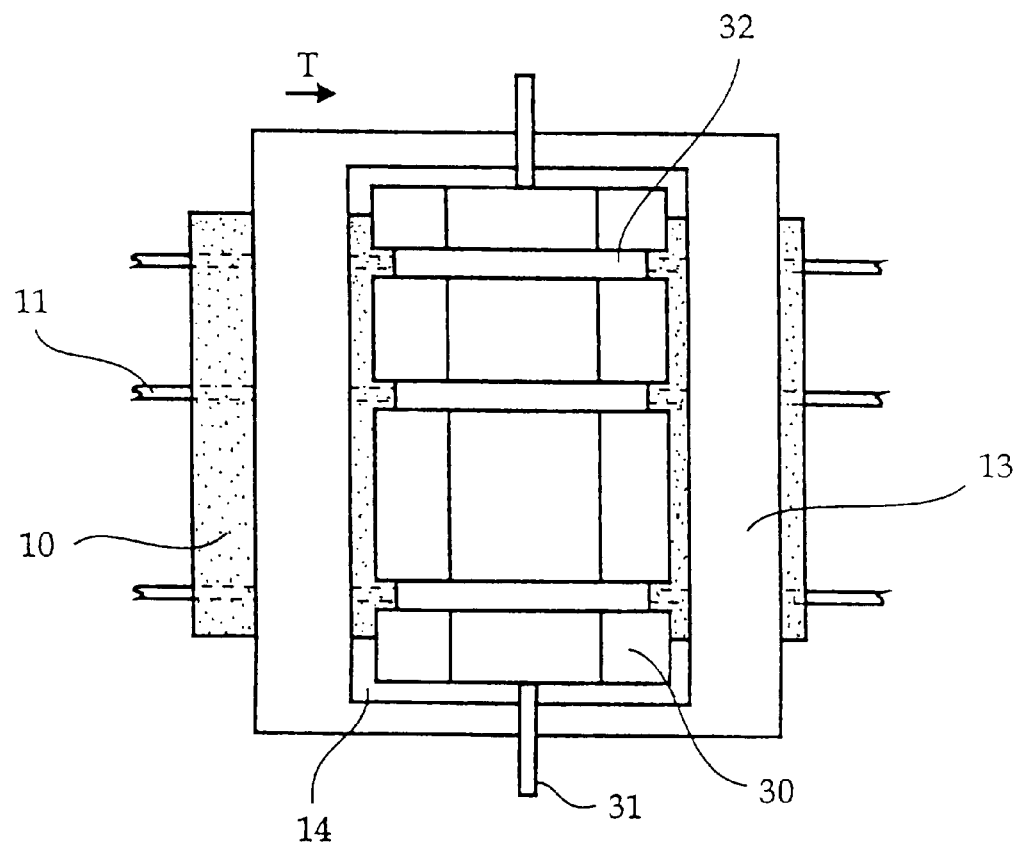
FIG. 4 shows a schematic diagram of the preferred embodiment with transport belts and a guiding plate from below.

FIG. 4 shows the preferred embodiment with upper transport belts 11 and guiding plate 13, regarded from below. Guiding plate 13 functionally replaces lower transport belts 12 according to FIG. 3. During transport through the apparatus, sheet material 10 is transported by upper transport belts 11 across guiding plate 13. Here, too, transport belts 11 are decoupled from roll 30 by free-running rollers 32. Guiding plate 13 has gap 14 through which roll 30 comes in contact with sheet material 10.

Figure 5:
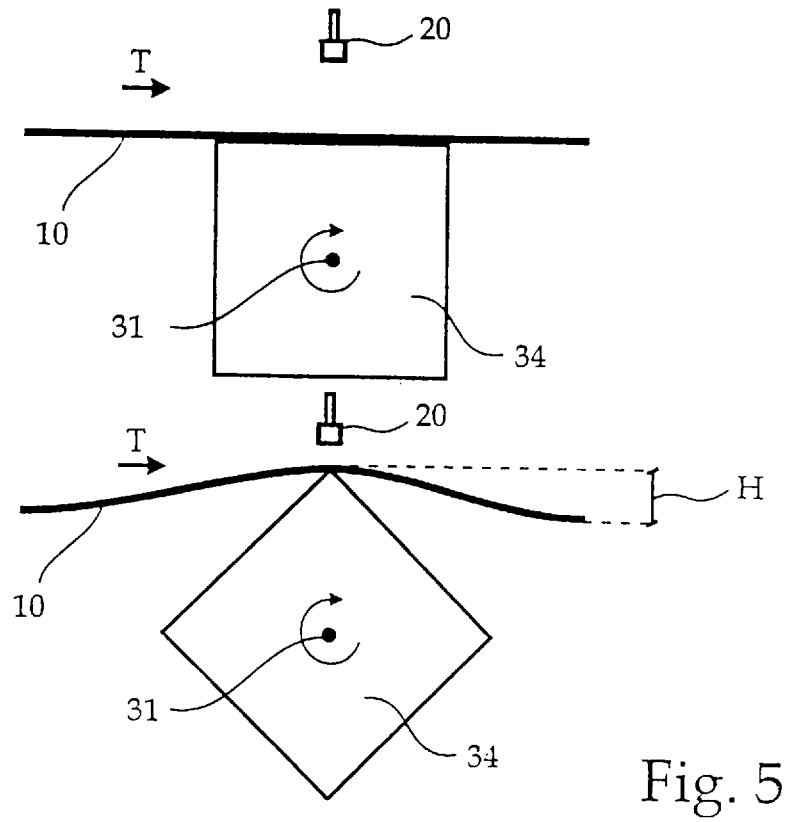
FIG. 5 shows a schematic diagram of a variation of the preferred embodiment.

FIG. 5 shows a variation of the preferred embodiment with four-cornered roll 34. In contrast to hexagonal roll 30 shown in FIG. 1, lifting height H of four-cornered roll 34 is greater than lifting height H of hexagonal roll 30. If the other parameters are constant, the sounds produced by four-cornered roll 34 are thus louder than those from hexagonal roll 30. In order to ensure a constant contact frequency in both variants of the embodiment, the rotary frequency of four-cornered roll 34 must be increased accordingly over hexagonal roll 30. The rotary frequency can only be varied within certain limits due to the mechanical problems occurring at high rotary frequencies, however, so that it is necessary to optimize the parameters in order to produce sufficiently loud sounds at a given contact frequency.

Figure 6:
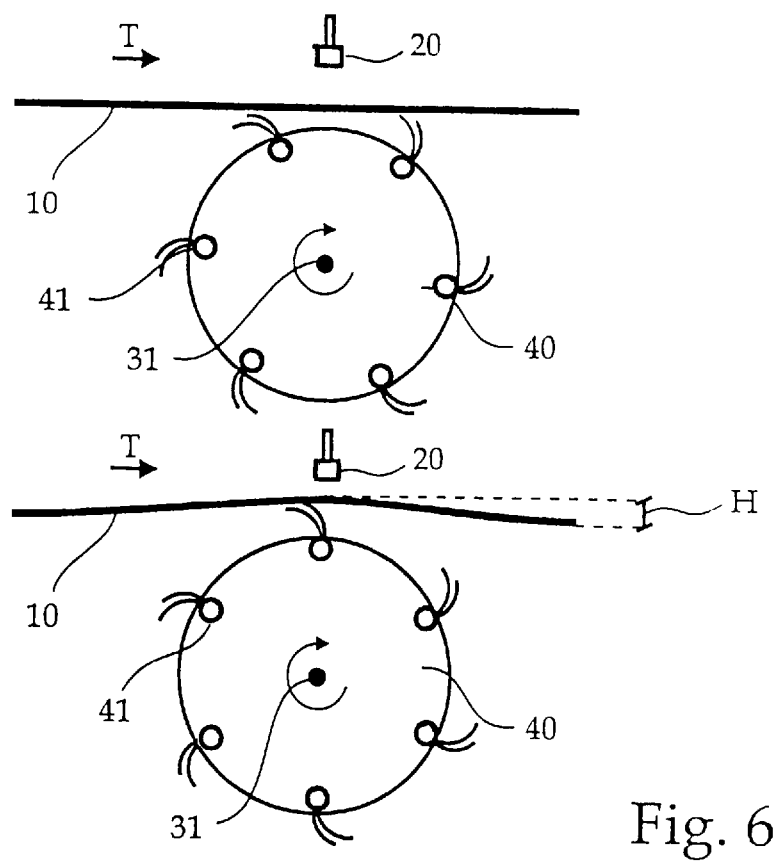
FIG. 6 shows a schematic diagram of a second embodiment of the invention.

FIG. 6 shows a second embodiment of the invention wherein brushes 41 are disposed in rotational symmetry on rotating roll 40. Brushes 14 are preferably executed to be movable on their own axes, so that brushes 41 swing outward due to the centrifugal force occurring upon rotation of roll 40. The sounds necessary for determining the stiffness of the sheet material are produced here by the periodic contact of brushes 41 against sheet material 10. The parameters described for the preferred embodiment of the invention, and the shown variations, can be easily transferred to this embodiment so that another description can be dispensed with.

Figure 7:
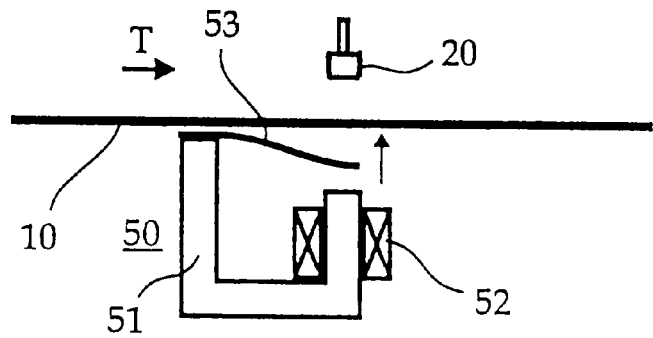
FIG. 7 shows a schematic diagram of a third embodiment of the invention.
Figure 7:
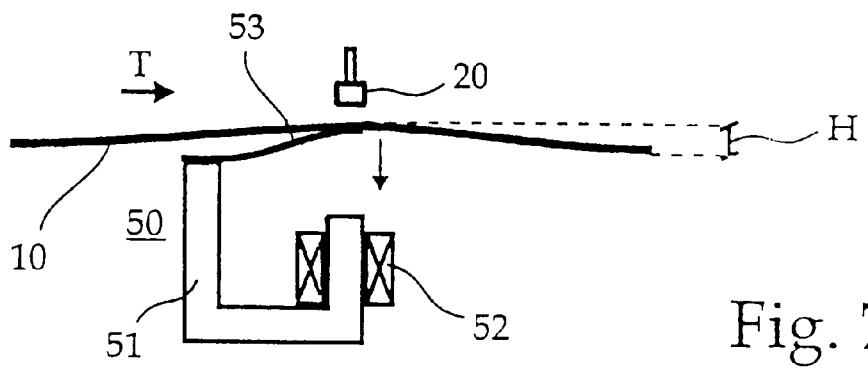

FIG. 7 shows a third embodiment of the invention wherein the device for producing sounds has as mechanical means electromagnet 50 with yoke 51, coil 52 and movable tongue 53. By applying an alternating voltage to coil 50 one causes movable tongue 53 to vibrate. The sounds are produced by periodic touching of sheet material 10 by tongue 53. The vibrating frequency of movable tongue 53 corresponds to the frequency of the applied alternating voltage. Lifting height H can be varied by the maximum voltage difference of the alternating voltage.

Figure 8:
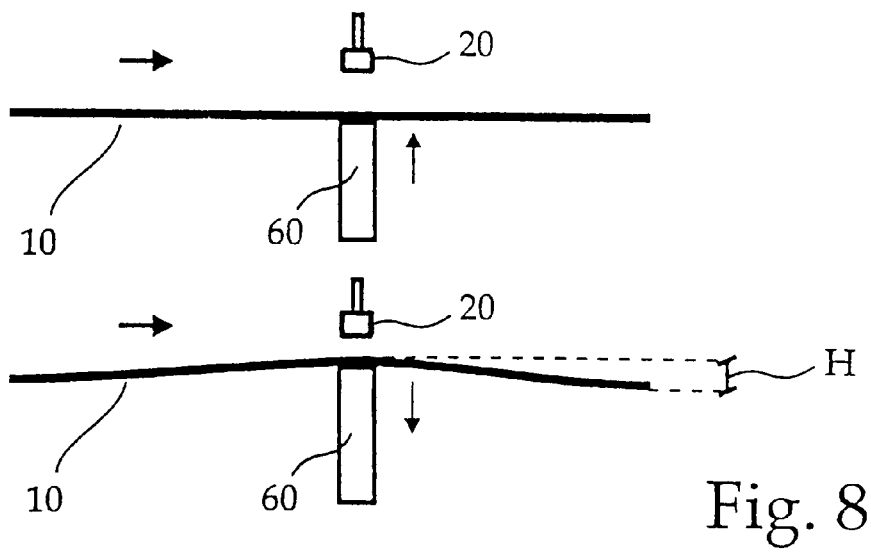
FIG. 8 shows a schematic diagram of a fourth embodiment of the invention.

FIG. 8 shows a fourth embodiment of the invention wherein the mechanical means for producing sounds have piezoelectric element 60. By applying an alternating voltage one can vary the volume expansion of piezoelectric element 60 in the direction perpendicular to the plane of the sheet material. The frequency of expansion of piezoelectric element 60 corresponds to the frequency of the applied alternating voltage. The extent of expansion of piezoelectric element 60 depends on the maximum voltage difference of the alternating voltage, but is relatively low. This leads merely to small lifting height H of sheet material 10 and thus also to a low volume of produced sounds.

Figure 9:
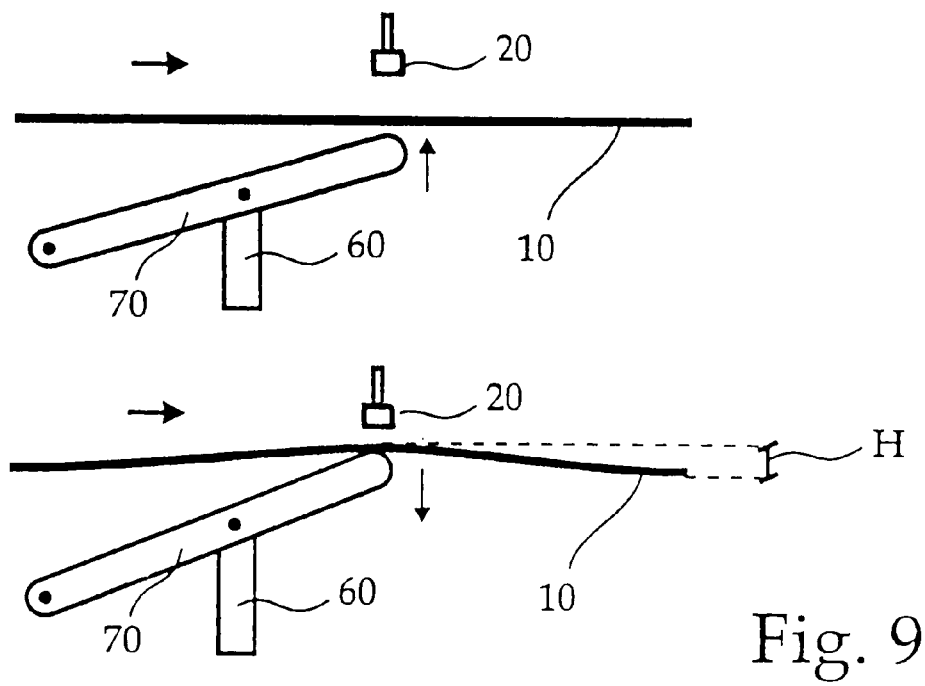
FIG. 9 shows a schematic diagram of a development of the fourth embodiment of the invention.

A method for increasing lifting height H of sheet material 10 is shown in FIG. 9. It consists in providing additional lever system 70 connected with piezoelectric element 60 and used for increasing the expansion of piezoelectric element 60 so as to obtain desired lifting height H.

Alternatively one can use for example so-called bimorphic piezoelectric elements 60 to increase lifting height H of sheet material 10. In such bimorphic piezoelectric elements 60 at least two piezoelectric elements 60 are firmly interconnected and the expansion of piezoelectric elements 60 is converted into a bending of piezoelectric elements 60. Bimorphic piezoelectric elements 60 can produce lifting heights H of several millimeters.

Figure 10:
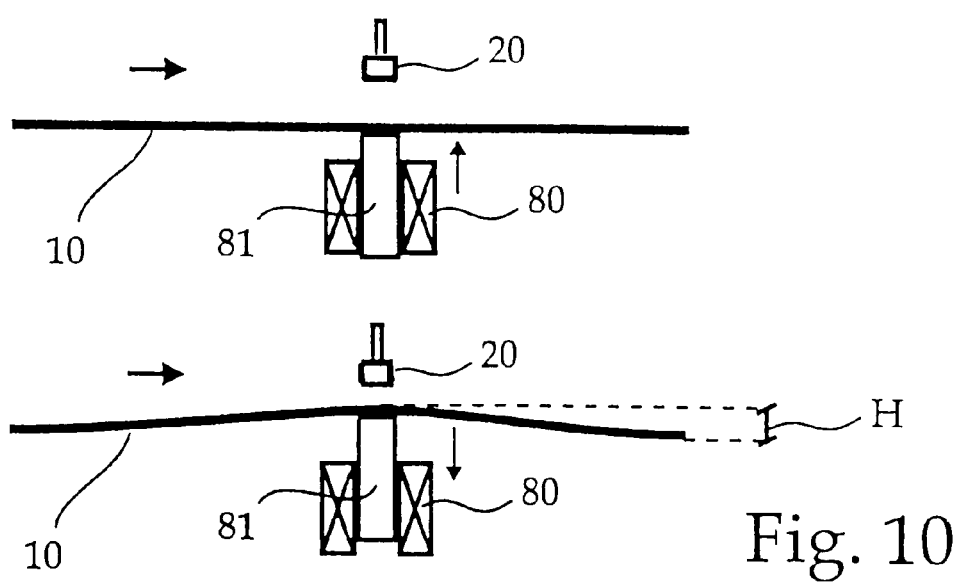
FIG. 10 shows a schematic diagram of a fifth embodiment of the invention.

FIG. 10 shows a fifth embodiment of the invention wherein the mechanical means for producing the sounds have coil 80 with movable magnetic core 81. When one applies an alternating voltage to the coil, movable magnetic core 81 vibrates at the frequency of the alternating voltage. The sounds arise through periodic touching of sheet material 10 by magnetic core 81. The excursion of movable core 81 and thus lifting height H of sheet material 10 can be influenced by the maximum voltage difference of the alternating voltage.

In addition to the above-described embodiments, it is of course possible for the expert with knowledge of the basic idea of the invention to develop variations of the described embodiments or new embodiment based on the idea of the invention. It is specifically possible to transfer the transport devices explained for the preferred embodiment to the other embodiments analogously.

All known methods of analog or digital signal processing can be used for evaluating the detected sounds.

We claim:

1. In an apparatus for determining the stiffness of sheet material such as bank notes, including
   a device for producing sounds using the sheet material,
   a detector for detecting the produced sounds,
   an evaluating device for determining the stiffness of the sheet material from the detected sounds, the improvement comprising:
   said device for producing sounds comprising a mechanical device arranged so that it (30, 34, 40, 41, 50, 60, 70, 80, 81) periodically touches the sheet material (10) and periodically raises it by a lifting height (H) above a non-raised height and permits the sheet material to be periodically lowered to its non-raised height to thereby cause it to vibrate.

2. The improvement of claim 1 wherein the mechanical device comprises a rotating roll (30, 34) with a selected number (N) of rotationally symmetric corners.

3. The improvement of claim 1 wherein the mechanical device comprises a rotating roll (40) with brushes (41) disposed in rotational symmetry thereon.

4. The improvement of claim 2, wherein the sheet material is transported through the apparatus by means of a transport device (11, 12), and the driving axle (31) of the rotating roll (30, 34, 40) is disposed perpendicular to the transport direction (T) of the sheet material.

5. The improvement of claim 4, wherein the circumferential speed of the roll (30, 34, 40) is in the direction of transport (T) of sheet material and is greater than or equal to the transport speed of the sheet material.

6. The improvement of claim 4, wherein the transport device has upper and/or lower transport belts (11,12) decoupled from the driving axle (31) by free-running rollers (32,33).

7. The improvement of claim 6, wherein the transport device has a guiding plate (13) with a gap (14) through which the roll (30, 34, 40) comes in contact with the sheet material (10).

8. The improvement of claim 1, wherein the mechanical device comprises an electromagnet (50) with a movable tongue (53).

9. The improvement of claim 1, wherein the mechanical device comprises a piezoelectric element (60).

10. The improvement of claim 9, wherein the mechanical device comprises an additional level system (70) connected with the piezoelectric element (60).

11. The improvement of claim 9, wherein the mechanical device comprises at least one further piezoelectric element (60) and the piezoelectric elements (60) are firmly interconnected so that the expansion of the piezoelectric elements (60) is converted into a bending of the piezoelectric elements.

12. The improvement of claim 1, wherein the mechanical device comprises a coil (80) with a magnetic core (81).

13. In a method for determining the stiffness of sheet material such as bank notes, including producing sounds using the sheet material, and detecting the produced sounds of the sheet material, whereby the stiffness of the sheet material is determined from the detected sounds of the sheet material, the improvement comprising:

producing the sounds using the sheet material (10) by periodic touching the sheet material (10) to periodically raise the sheet material a lifting height (H) above a non-raised height and permitting the sheet material to periodically drop to its non-raised height to thereby cause the sheet to vibrate.

* * * * *